United States Patent
Essayem et al.

(10) Patent No.: US 8,704,003 B2
(45) Date of Patent: Apr. 22, 2014

(54) METHOD FOR PREPARING A MIXTURE OF BIOFUELS

(75) Inventors: Nadine Essayem, Saint Just Chaleyssin (FR); Rodrigo Lopes de Souza, Rio de Janeiro (BR); Berna Hamad, Villeurbanne (FR); Gilbert Sapaly, Lyons (FR); Paulo Gustaro Pries de Oliveira, Rio de Janeiro (BR); Wilma Gonzalez, Rio de Janeiro (BR)

(73) Assignees: Centre National de la Recherche Scientifique (C.N.R.S.), Paris (FR); Universite Claude Bernard Lyon I., Villeurbanne (FR)

( * ) Notice: Subject to any disclaimer, the term of this patent is extended or adjusted under 35 U.S.C. 154(b) by 218 days.

(21) Appl. No.: 12/991,314

(22) PCT Filed: May 5, 2009

(86) PCT No.: PCT/FR2009/050834
§ 371 (c)(1),
(2), (4) Date: Jan. 31, 2011

(87) PCT Pub. No.: WO2009/141564
PCT Pub. Date: Nov. 26, 2009

(65) Prior Publication Data
US 2011/0146137 A1    Jun. 23, 2011

(30) Foreign Application Priority Data

May 5, 2008  (FR) ...................................... 08 02491

(51) Int. Cl.
*C07C 41/01*    (2006.01)
(52) U.S. Cl.
USPC ........................................... 568/579; 44/307
(58) Field of Classification Search
USPC ........................................... 44/307; 568/579
See application file for complete search history.

(56) References Cited

U.S. PATENT DOCUMENTS

| 5,908,946 | A | 6/1999 | Stern et al. |
|---|---|---|---|
| 6,015,440 | A | 1/2000 | Noureddini |
| 2007/0066838 | A1 | 3/2007 | Hillion et al. |
| 2007/0112212 | A1 | 5/2007 | Hillion et al. |
| 2007/0238905 | A1 * | 10/2007 | Arredondo et al. ........... 568/672 |
| 2007/0260078 | A1 * | 11/2007 | Bhat et al. ...................... 554/174 |
| 2007/0283619 | A1 | 12/2007 | Hillion et al. |
| 2009/0013591 | A1 | 1/2009 | Bradin et al. |
| 2009/0126262 | A1 * | 5/2009 | Asthana et al. ................. 44/388 |

FOREIGN PATENT DOCUMENTS

WO    WO 00/13792    3/2000

OTHER PUBLICATIONS

International Search Report for PCT/FR2009/050834.
Bokade V V et al: "Synthesis of Bio-Diesel and Bio-Lubricant by Transesterification of Vegetable Oil with Lower and Higher Alcohols Over Heteropolyacids Supported by Clay (K-10)", Process Safety and Environmental Protection, Institution of Chemical Engineers, Rugby, GB, vol. 85, No. 5, (Jan. 1, 2007), pp. 372-377.
Morin et al: "Transesterification of rapeseed oil with ethanol", Applied Catalysis A: General, Elsevier Science, Amsterdam, NL vol. 330, (Sep. 17, 2007), pp. 69-76.

* cited by examiner

*Primary Examiner* — Monique Cole
(74) *Attorney, Agent, or Firm* — B. Aaron Schulman, Esq.; Stites & Haribson, PLLC

(57) ABSTRACT

The invention relates to a method of preparing a mixture of biofuels comprising fatty acid esters and at least one mixture of glycerol ethers from fatty substances that may contain free fatty acids and ethanol comprising: a) a step of transesterification of a vegetable or animal oil by ethanol in the presence of a catalyst based on at least one alkali metal salt or ammonium heteropolyacid salt characterized by differential heat of adsorption of ammonia which is greater than or equal to 150 kJ/mol, stable at T>150.degree. C., in order to obtain fatty acid esters and glycerol, and, b) a step of etherification of the glycerol formed during step a) by the alcohol used in step a) in the presence of the catalyst from step a) in order to obtain at least one ether of the glycerol, said steps a) and b) taking place simultaneously, in one and the same reactor.

10 Claims, No Drawings

METHOD FOR PREPARING A MIXTURE OF BIOFUELS

The production of methyl or ethyl ethers of fatty acids (biodiesel) during the transesterification reaction of a fatty substance inevitably produces glycerol. The upgrading thereof is a determining factor for the equilibrium of the biodiesel field.

Furthermore, glycerol ethers are also potential fuel additives which may go into the diesel fuel pool.

The most common transesterification processes use a basic homogeneous catalysis, for example the processes described in patent application US 2003/0032826 (University of Nebraska). The products of the reaction must then undergo steps of neutralization, washing and separation in order to obtain the fatty acid esters, but also the glycerol of sufficient purity in order to be sold.

Continuous or batch processes for the transesterification of oils by monoalcohols that require heterogeneous catalysis have appeared more recently. Such as, for example, the processes described in patent applications U.S. Pat. No. 5,908,946 (IFP) or US 2004/0112212 (IFP), in which the glycerol obtained, of higher purity, is decanted from the reaction medium then removed.

The processes for transesterification by ethanol are less widespread. Transesterification by ethanol is generally less effective. In particular, via basic catalysis, transesterification by ethanol is slower than with methanol, methanol being more acidic than ethanol. Furthermore, one of the reasons mentioned relates to the better solvent power of ethanol which is responsible for the poor separation of the glycerin from the reaction medium. Furthermore, since the transesterification is a balanced reaction, the solubilization of the glycerol in the reaction medium may have the result of limiting the progress of the reaction. This high solvent power of the ethanol furthermore has a drawback at the end of the reaction; it is more difficult to separate the glycerin from the reaction medium by decantation, see US 2007/0112212 (IFP).

To overcome this major difficulty, two-step processes are thus proposed, for example in US 2007/0066838 A1 (IFP), in order to prepare ethyl esters of linear monocarboxylic acids from vegetable or animal oil comprising a transesterification by methanol in a first step then a second transesterification step in which the reaction medium produced is reacted with ethanol.

The transesterification of vegetable oil by alcohols in the presence of heteropoly acids has also been described by V. V. Bokade et al., Trans IChemE, Part B, Process safety and Environmental Protection (2007), 85 (B5), 372-377. The authors studied the transesterification reaction of a vegetable oil with a supported heteropoly acid catalyst. Screening of various catalysts enabled them to distinguish a specific catalyst that gives good conversion yields with methanol: 10% of dodecatungstophosphoric acid on clay. This catalyst was then studied for the transesterification of an oil with various alcohols; it is noticed from this study (table 5) that the yields are higher with methanol than with ethanol (respectively 84 and 80% conversion). The authors also suggest that it might be possible to continue the reaction and to form glycerol ethers.

More recently, the transesterification of rapeseed oil with ethanol in the presence of strong Brønsted acid catalysts (heteropoly acids of Keggin structure) has been described by N. Essayem et al. Appl. Catal. A: General 330 (2007) 69-76. The separation of the glycerol is not however addressed in this article. The reaction described has a yield of less than 55%.

The glycerol may be upgraded, for example as a synthesis intermediate and may be used as an emulsifier, plasticizer, solvent, etc. Numerous studies are under way for finding new applications for glycerol, but these depend on the cost price of the glycerol, which is a function of its degree of purity. The economic advantage of upgrading the glycerol as such is obvious only if the glycerol is of low cost, therefore is not very purified.

However, the most advantageous upgrading is an upgrading of the latter in the field of fuels or biofuels.

Glycerol ethers are potential fuel additives which may be incorporated into the formulation of fuels. This application is even more advantageous since European Directives will impose the use of 5.75% of biofuels in the transport industry in 2010. International application WO 2007/061903 A1 (CPS Biofuels) and U.S. Pat. No. 5,308,365 (ARCO Chemical Technology) describe fuel compositions comprising glycerol ethers.

It is known from WO 2007/061903 A1 (CPS Biofuels) that the addition of glycerol ethers to the bioethanol makes it possible to reduce the vapor pressure of the fuel obtained. Furthermore, glycerol ethers may replace conventional oxygenated additives of the MTBE type. They also make it possible to reduce particulate emissions and then reduce the viscosity of the biodiesel fuel. It is also reported that the presence of the hydroxyl group of partially etherified glycerol ethers may make it possible to incorporate small amounts of water into the fuels, which could reduce $NO_x$ emissions.

From WO 2005/093015 (IFP), it is known that glycerol ethers make it possible to make the glycerol soluble in the biodiesel. In this patent application, the obtaining of a mixture of mono-, di- and triglycerol ethers is described, the mixture being soluble in the biodiesel.

Concentrations of 1 to 20% in diesel fuels and up to 50% in gasolenes are reported and, for example, the incorporation into the biodiesel of the whole of a mixture of mono-, di- and tri-tert-butyl ethers having the average composition equivalent to a di-tert-butyl ether.

It is also known that the addition of glycerol ethers to the biodiesel makes it possible to reduce its viscosity and its "cloud point" (U.S. Pat. No. 6,015,440 (University of Nebraska)).

U.S. Pat. No. 6,015,440 (University of Nebraska) and the international application WO 2005/093 015 (IFP) report the etherification of glycerol with isobutylene via an acid catalyst. The manufacture of t-butyl ethers of glycerol from tert-butanol is also described. Furthermore, international application WO 2007/113 776 (Procter & Gamble) describes a process for converting glycerol to alkyl glycerol ethers catalyzed by Lewis or Brønsted acids. More specifically, the etherification of glycerol by methanol or isopropanol in the presence of an Amberlyst resin is reported.

Biodiesel production processes have been described that use two separate steps, including a step of etherification of the glycerol. For example, in US 2007/0260078 (Ramanath et al.), the first step is a transesterification reaction of a vegetable oil by an alcohol, in the presence of a double metal cyanide catalyst, the reaction medium is then cooled and reacted with the alcohol in the presence of an Amberlyst catalyst. The reaction gives rise to the formation of a biodiesel comprising ethyl esters of fatty acids and triethyl ethers of glycerol. However, Amberlyst catalysts are very sensitive to temperature and degrade at high temperatures, furthermore this process has two steps which is a drawback for an industrial application.

Moreover, it has been demonstrated (see WO 2007/061903) that the presence of the hydroxyl group, therefore of monoethers or diethers of glycerol, was more advantageous. As described above, it was suggested in V. V. Bokade et al., that it could be possible to continue the reaction. However, this suggestion is not demonstrated in the least. Furthermore, the reaction described in this publication has a significant monoglyceride and diglyceride selectivity (35% for the reaction with ethanol), however to continue the reaction a lower amount of monoglyceride and diglyceride is required.

This transesterification process also has the drawback of using supported heteropoly acid catalysts which are leachable catalysts and the activity and the strength of which depend on the nature of the support and on the acid loading on the support.

The objective of the present invention is a method for producing a biodiesel by transesterification and etherification reaction, in a single step, of a vegetable oil with ethanol.

Another objective of the present invention is a method for producing a biodiesel that makes it possible to upgrade the secondary products formed and in particular glycerol.

Another objective of the present invention is a biofuel comprising ethyl esters of fatty acids and a mixture of ethyl ethers of glycerol.

The inventors have surprisingly discovered that the family of heterogeneous strong Brønsted acid catalysts (heteropoly acid salts) makes it possible to transesterify an oil and to simultaneously produce ethers of glycerol without isolating the intermediate glycerol. Surprisingly, the inventors have discovered that it was possible to upgrade all the secondary products that are formed during the reaction and in particular to etherify the glycerol, in a single step, at the same time as the transesterification reaction.

The transesterification of oils by an alcohol generates in situ glycerol in the reaction medium, which is converted to alkyl ethers of glycerol in the presence of a heterogeneous acid catalyst capable of catalyzing the transesterification and etherification reactions by the same alcohol.

The use of heterogeneous acid catalysis compared to the conventional methods of basic homogeneous catalysis exhibits a major advantage in the upgrading of oils which are potentially acidic, for example the wasted oils which may have a high content of free acids and which may contain greater or smaller traces of water. Indeed, when water is capable of adversely affecting the rate of the reaction this will not be a major problem as in the case of a conventional basic homogeneous catalysis in which the presence of water promotes the hydrolysis of the oil to free acids, the latter, in the presence of the alkali metal cations of the homogeneous base, form soaps which produce emulsions in the reaction medium, etc. But also, a basic solid catalyst will be capable of exhibiting deactivation by adsorption of the free fatty acids at its surface in the event of oils having a high acidity index being used.

Since the fatty acid esters and the glycerol ethers are components of biofuels, the whole of a fatty substance may be converted to diesel fuel without having to separate and purify the glycerol, which is an enormous advantage in terms of cost compared to the methods of the prior art.

Indeed, the method according to the invention makes it possible to eliminate the expensive steps of isolating and of purifying the glycerol.

Furthermore, the glycerol ethers formed are the most favorable with respect to the reduction of $NO_x$ emissions.

Furthermore, by simply considering that the glycerol produced by transesterification of the oils represents 10% by weight of the fatty acid esters produced, the method according to the invention enables an increase in the yield of more than 15% by weight.

Moreover, the use of the same catalyst for carrying out the transesterification and the etherification on the one hand, and of the same reactant, namely an alcohol, for carrying out both reactions, also represents an economic advantage. It is not necessary to use another reactant of olefin type for synthesizing the glycerol ethers.

Furthermore, the solid catalyst used does not undergo the leaching observed with the catalysts based on supported acids, withstands washing and can therefore be easily isolated from the biofuel formed.

Furthermore, since the method does not require a glycerol separation step, it enables an alcohol having a high solvent power, such as ethanol, to be used which is advantageous since this alcohol is "bio-sourced", is a by-product of agricultural waste recycling processes, is available at low cost and is not toxic compared to methanol.

Finally, the method enables all the secondary products which may be formed during the reaction to be upgraded.

The present invention relates to a method for preparing a mixture of biofuels comprising fatty acid esters and at least one mixture of glycerol ethers from fatty substances and ethanol, comprising:

a) a step of transesterification of a vegetable or animal oil by ethanol in the presence of a catalyst based on at least one alkali metal or ammonium heteropoly acid salt characterized by a differential heat of adsorption of ammonia greater than or equal to 150 kJ/mol, in order to obtain fatty acid esters and glycerol; and b) a step of etherification of the glycerol formed during step a) by the ethanol used in step a) in the presence of the catalyst from step a) in order to obtain at least one glycerol ether, said steps a) and b) taking place simultaneously, in one and the same reactor.

In one embodiment, the catalyst based on at least one alkali metal or ammonium heteropoly acid salt is insoluble in the reaction medium and the biofuel obtained.

In one embodiment, the catalyst is a catalyst based on at least one alkali metal heteropoly acid salt.

In one embodiment, the catalyst is a catalyst based on at least one ammonium heteropoly acid salt.

In one embodiment, the differential heat of adsorption of ammonia is greater than 170 kJ/mol.

In one embodiment, the differential heat adsorption of ammonia is greater than 190 kJ/mol.

The glycerol that acts as the reactant for step b) corresponds to a product from step a). It is a non-isolated intermediate product. The method according to the invention advantageously makes it possible not to isolate and purify the glycerol in order to convert it to ethyl ether of glycerol (component of the biofuel).

The expression "steps a) and b) take place simultaneously" means that the two reactions take place simultaneously in the reaction medium ("one-pot" reaction), the glycerol formed during step a) being converted to glycerol ether as soon as it is formed. The inventors have surprisingly discovered that, generally, the reaction medium obtained at the end of the process may be free of glycerol if the conversion is continued by means known to the person skilled in the art, namely increase of the reaction time, of the mass of catalyst or by recirculation of the reaction medium.

The term "glycerol", also known as "glycerin", denotes 1,2,3-propanetriol. The glycerol may be pure glycerol, but also glycerol comprising impurities, especially water, inorganic salts (chloride, phosphate, sulfate, acetate), organic compounds (fatty acids, fatty acid esters, derivatives of glycerides, etc.). These impurities may represent from 5 to 95% by weight relative to the weight of the glycerol. The glycerol may in particular be the crude glycerol obtained by transesterification of vegetable or animal oils within the context of biodiesel production. The expression "crude glycerol" denotes the glycerol obtained by simple decantation of the reaction medium at the end of the transesterification of vegetable or animal oils.

The expression "etherification of glycerol" denotes the chemical reaction which makes it possible to convert glycerol to glycerol ethers.

The expression "glycerol ethers" denotes the mono-, di- and triethers of glycerol. In the case of mono- and diethers of glycerol, the ether function(s) may be located at any one of the 1, 2 or 3 position(s). The reaction for formation of the various glycerol ethers follows a successive path: the monoether then the diether and the triether of glycerol are produced: it is possible to promote the formation of the diether and triether by increasing the reactants/catalyst contact time (for example by increasing the mass of catalyst or the reaction time) or it is possible to recirculate the product of the reaction in order to increase the glycerol conversion and move towards the production of triethers of glycerol.

The mixture of glycerol ethers obtained simply has to be soluble in the biodiesel or in the other fuels such as diesel (from oil) or gasoline (or even bioethanol) into which it will be added.

In one preferred embodiment, the expression "glycerol ethers" is understood to mean the monoethers and diethers of glycerol.

The term "ethanol" denotes in particular absolute and/or anhydrous ethanol.

The expression "heteropoly acid" is understood to mean a compound constituted of hydrogen and oxygen with metallic elements (such as tungsten, molybdenum or vanadium) and non-metallic elements, generally from the p block of the Periodic Table (such as silicon, phosphorus or arsenic).

In one embodiment, the invention relates to a method, characterized in that the glycerol ethers are chosen from the monoethers and diethers of glycerol.

In one embodiment, the invention relates to a method, in which the molar ratio between the ethanol and the vegetable or animal oil is between 1 and 50, preferentially between 3 and 20.

In one embodiment, the invention relates to a method for the etherification of glycerol by ethanol comprising a step of reaction between glycerol and ethanol in the presence of a catalyst based on at least one alkali metal or ammonium heteropoly acid salt characterized by a differential heat of adsorption of ammonia greater than or equal to 150 kJ/mol.

In one embodiment, the invention relates to methods, characterized in that the catalyst based on at least one alkali metal or ammonium heteropoly acid salt has a differential heat of adsorption of ammonia greater than or equal to 170 kJ/mol, preferably greater than or equal to 190 kJ/mol.

Among the alkali metal or ammonium heteropoly acid salts, use may advantageously be made of an alkali metal or ammonium salt of a solid heteropoly acid having the general formula:

$$H_k X_l M_m O_n \cdot xH_2O$$

in which:
X represents a heteroatom chosen from the group constituted by the following elements: P, Si, Ge, B or As;
M represents a peripheral metallic element chosen from the group constituted by W, Mo or V;
l is the number of heteroatoms and represents 1 or 2;
k is the number of hydrogen atoms and is between 1 and 10;
m is the number of peripheral metallic atoms W, Mo, V and is between 1 and 20;
n is the number of oxygen atoms and is between 2 and 62;
x is the number of molecules of water of hydration and is between 0 and 40, preferably between 6 and 30.

In one embodiment, the salts of solid, strong Brønsted acid heteropoly acids are chosen from the group constituted by the salts of the heteropoly acids chosen from the group constituted by $H_3PW_{12}O_{40} \cdot 24H_2O$, $H_4SiW_{12}O_{40} \cdot 24xH_2O$, $H_6P_2W_{18}O_{62} \cdot 24H_2O$, $H_5BW_{12}O_{40} \cdot 30H_2O$, $H_5PW_{10}V_2O_{40} \cdot xH_2O$, $H_3PMo_{12}O_{40} \cdot 28H_2O$, $H_4SiMo_{12}O_{40} \cdot 13H_2O$, $H_3PMo_6V_6O_{40} \cdot xH_2O$ or $H_5PMo_{10}V_2O_{40} \cdot xH_2O$.

The use of a heteropoly acid in salt form has numerous advantages, in particular from an industrial viewpoint, they make it possible, on the one hand, unlike supported heteropoly acids (used especially by Bokade et al.) to avoid any problem of leaching of the active phase. Moreover, unlike supported heteropoly acids, the activity of the heteropoly acid salts does not depend on the support or on the acid loading on the support. In one embodiment, the salts are alkali metal salts chosen from $Cs^+$, $K^+$ or $Rb^+$, or ammonium ($NH_4^+$) salts.

In one embodiment, the salt is $Cs^+$.

In another embodiment, the salt is a $K^+$.

In another embodiment, the salt is an $Rb^+$.

In a last embodiment, the salt is an ammonium ($NH_4^+$) salt.

In the case of the etherification process, these catalysts specifically make it possible to observe conversions of greater than 40%.

The expression "differential heat of adsorption of ammonia" denotes the molar heat released by the adsorption of infinitesimal doses of ammonia, at constant temperature, on the catalyst initially under vacuum in a Tian-Calvet calorimeter.

The values of the differential heats of adsorption of ammonia correspond to the value of the plateau of the curve representing the variation of the differential heats (Q diff kJ·mol$^{-1}$) as a function of the amount of ammonia adsorbed if the acidic solid has homogeneous sites in force. If the differential heats decrease with the ammonia coverage, the value considered is the average of the differential heats of adsorption at 50% ammonia coverage.

The average values obtained for the acid catalysts are collated in the following table:

| Catalyst | Qdiff (kJ/mol$^{-1}$) |
| --- | --- |
| $Cs_2HPW_{12}O_{40}$ | 190-210 |
| $(NH_4)_{2.5}H_{0.5}PW_{12}O_{40}$ | 200 |
| $H_3PW_{12}O_{40}$ | 195 |
| HPA*/charcoal | 150 |
| HPA/SiO$_2$ | 160 |
| HPA/Nb$_2$O$_5$ | 135 |
| HPA/ZrOH | 130 |
| ZrO$_2$/SO$_4$ | 140 |
| Nb$_2$O$_5$ calcined at 400° C. | 150 |
| tungstated ZrO$_2$ | 130 |
| Amberlyst A15 | 135 |

*HPA for 40% $H_3PW_{12}O_{40}$

The term "biofuel" denotes a fuel produced from renewable organic materials.

The expression "mixture of biofuels" is understood to mean a mixture of biofuels or a "bio-sourced" base for the formulation of other fuels.

The expression "fatty acids" denotes aliphatic carboxylic acids having a carbon-based chain of 4 to 28 carbon atoms.

The expression "fatty substances" is understood to mean natural fatty substances of any origin.

The expression "vegetable or animal oil" denotes oil of animal or vegetable origin, such as microalgae oil, *Pongamia pinnata* (or Karanja) oil, Jatropha oil, palm oil, sunflower oil, rapeseed oil, almond oil, arachis oil, coconut oil, linseed oil, corn oil, olive oil, grapeseed oil, castor oil, sesame oil or mustard oil, but also wasted oils that are rich in free acids. These oils contain or are constituted of acyl glycerols, also known as glycerides, which are esters of fatty acids and of glycerol. There are three subclasses of acyl glycerols: monoglycerides, diglycerides and triglycerides. The prefixes mono, di, and tri are used according to whether the esterification relates to 1, 2 or 3 hydroxyl groups of the glycerol.

The expression "transesterification of the vegetable or animal oil by an alcohol" denotes the chemical reaction of the triglycerides with an alcohol in the presence of the catalyst in order to obtain esters of fatty acids and glycerol.

The expression "etherification of glycerol by an alcohol" denotes the reaction of glycerol and an alcohol in the presence of catalyst to obtain at least one glycerol ether, which may be a monoether, diether or triether of glycerol. Generally, a mixture of these ethers is obtained.

In one embodiment of the methods according to the invention, the molar ratio between the ethanol and the vegetable or animal oil is between 1 and 50, in particular between 3 and 20, for example 4, 6, 12 or 18.

Indeed, these molar ratios make it possible to observe conversions of greater than 80% or even greater than 95% for step a), and of the order of 50% for step b).

In one embodiment, the methods are carried out at a temperature between 100 and 300° C., especially 150 to 250° C., in particular around 200° C., and at a pressure between 5 and 100 bar, especially 10 to 75 bar, in particular 10 to 50 bar, more particularly between 20 and 30 bar.

These reaction conditions are particularly suitable for implementing the methods according to the invention, in particular the etherification of glycerol by ethanol which is energetically demanding: it requires the use of a catalyst of alkali metal or ammonium heteropoly acid salt type at a reaction temperature of around 200° C. This temperature is considerably greater than the maximum operating temperature of acidic resins of Amberlyst type which is below 150° C. The use of such catalysts is advantageous because they are stable at these high temperatures, unlike other catalysts, such as the acidic resins of Amberlyst type. Furthermore, these catalysts are more reactive: by way of comparison, at 85° C. the cesium heteropoly acid salt is 4 times more active than Amberlyst 15 in relation to its more energetic sites.

According to a second aspect, the present invention relates to the use of a catalyst based on at least one alkali metal or ammonium heteropoly acid salt in order to carry out an etherification of glycerol by ethanol, in which the catalyst based on at least one alkali metal or ammonium heteropoly acid salt is characterized by a differential heat of adsorption of ammonia greater than 150 kJ/mol and stable at a temperature of 200° C.

In one embodiment, the catalyst is a catalyst based on at least one alkali metal heteropoly acid salt.

In one embodiment, the catalyst is a catalyst based on at least one ammonium heteropoly acid salt.

The invention also relates to the use of a catalyst based on at least one alkali metal or ammonium heteropoly acid salt, for simultaneously carrying out:

a transesterification of a vegetable or animal oil by ethanol in order to obtain ethyl esters of fatty acids and glycerol; and
an etherification of said glycerol by ethanol,
in which the catalyst based on at least one alkali metal or ammonium heteropoly acid salt is characterized by a differential heat of adsorption of ammonia greater than 150 kJ/mol, stable at a reaction temperature of 200° C.

In one embodiment, the catalyst is a catalyst based on at least one alkali metal heteropoly acid salt.

In one embodiment, the catalyst is a catalyst based on at least one ammonium heteropoly acid salt.

According to another aspect, the invention relates to a biofuel comprising ethyl esters of fatty acids and a mixture of ethyl ethers of glycerol.

In one embodiment, the invention relates to a biofuel comprising a mixture of monoethyl ethers and diethyl ethers of glycerol.

In one embodiment, said biofuel also comprises ethanol.

The invention will be described in greater detail by means of the following examples given by way of illustration.

COUNTER EXAMPLE 1

Etherification of Glycerol by Tert-Butanol or Ethanol in the Presence of Amberlyst 35

The reaction conditions were the following. The catalyst was Amberlyst A35 (m=0.39 g). 0.0275 mol of glycerol was used. The [ethanol or tert-butanol]/glycerol molar ratio was 4. The reaction time was 3 hours.

The results appear in table 1.

The conversion is calculated according to the following equation:

$$100 \times (Gly_o - Gly_f)/Gly_o$$

in which Gly represents the amount of glycerol, $Gly_o$ the amount of glycerol at the start of the reaction and $Gly_f$ the amount of glycerol at the end of the reaction. The selectivities and molar yields of glycerol derivatives are calculated as follows:

$$\text{Monoether Selectivity} = 100 \times \text{monoether}/(Gly_o - Gly_f)$$

$$\text{Diether Selectivity} = 100 \times \text{diether}/(Gly_o - Gly_f)$$

$$\text{Triether Selectivity} = 100 \times \text{triether}/(Gly_o - Gly_f)$$

$$\text{Monoether Yield} = 100 \times \text{monoether}/Gly_o$$

$$\text{Diether Yield} = 100 \times \text{diether}/Gly_o$$

$$\text{Triether Yield} = 100 \times \text{triether}/Gly_o$$

TABLE 1

| Alcohol | T(° C.) | Conversion (%) | Monoalkyl ether selectivity | Dialkyl ether selectivity | Trialkyl ether selectivity |
|---|---|---|---|---|---|
| tert-Butanol | 60 | 32 | 92.5 | 7.5 | — |
|  | 120 | 55 | 79 | 21 | — |
| Ethanol | 60 | 1 | — | — | — |
|  | 130 | 2.5 | 88 | 12 | — |
|  | 160 | 9 | 95 | 5 | — |

Conversion and selectivity of the reaction for etherification of glycerol by tert-butanol or ethanol catalyzed by Amberlyst A35. (alkyl=ethyl or t-butyl)

These experiments show that the etherification of glycerol by ethanol is energetically more demanding than the etherification by tert-butanol due to the greater acid nature of ethanol compared to the tertiary alcohol. This example shows the difficulty in carrying out the etherification of glycerol by ethanol with a standard etherification catalyst, acid resins. The conversion was not able to be improved by increasing the reaction temperatures since the acid resins are not stable at temperatures above 150° C.

The term HPA is understood to mean $H_3PW_{12}O_{40}$ and more precisely 40% by weight of $H_3PW_{12}O_{40}$ dispersed on supports.

EXAMPLE 2

Influence of the Nature of the Catalyst in the Etherification of Glycerol by Ethanol The reaction conditions were the following. 0.39 g of catalyst was used. 0.0275 mol of glycerol was used. The ethanol/glycerol molar ratio was 4. The temperature was 200° C. The reaction time was 6 hours.

The results appear in table 3. The most active catalysts under the conditions tested for the formation of ethyl ethers of glycerol are $HPA/SiO_2$, HPA/charcoal and $Cs_2HPW_{12}O_{40}$.

TABLE 3

Conversion and selectivity of the reaction for etherification of glycerol by ethanol according to the catalyst.

| Catalysts | Conversion (%) | Monoethyl ether selectivity | Diethyl ether selectivity | Triethyl ether selectivity |
|---|---|---|---|---|
| $Cs_2HPW_{12}O_{40}$ | 31 | 89 | 11 | — |
| HPA/charcoal | 35 | 95 | 15 | — |
| $HPA/SiO_2$ | 23 | 91 | 9 | — |
| $HPA/Nb_2O_5$ | ~0.5 | — | — | — |
| $ZrO_2/SO_4$ | 4.5 | 94 | 6 | — |
| $Nb_2O_5$ cal 400° C. | ~0.2 | — | — | — |

TABLE 3-continued

Conversion and selectivity of the reaction for etherification of glycerol by ethanol according to the catalyst.

| Catalysts | Conversion (%) | Monoethyl ether selectivity | Diethyl ether selectivity | Triethyl ether selectivity |
|---|---|---|---|---|
| tungstated $ZrO_2$ | ~0 | — | — | — |

The comparison of tables 2 and 3 shows that regardless of the catalyst used, the etherification of glycerol by ethanol is energetically more demanding than the etherification by tert-butanol and therefore more difficult to carry out. The results from tables 2 and 3 also show a variability of the activity of the supported heteropoly acids depending on the support.

EXAMPLE 3

Reaction Between Rapeseed Oil and Ethanol in the Presence of $Cs_2HPW_{12}O_{40}$ in Order to Produce, in a Single Step, Ethyl Esters of Fatty Acids (Biodiesel) and Glycerol Ethers (Fuel Ethers)

Tr=200° C. for 6 hours. (Tr=reaction time)

The reaction conditions were the following. 0.5 g of $Cs_2HPW_{12}O_{40}$ catalyst was used (pretreatment: 1 h under vacuum at 200° C.). 0.2047 mol of ethanol and 0.01144 mol (which corresponds to $Tri_o$ in the equations which follow) of rapeseed oil were used. The ethanol/ester molar ratio was 6 (the ethanol/oil molar ratio was 18). The rate of stirring was 500 rpm. The reaction time was 6 hours. The temperature was 200° C. The autoclave was pressurized at 17 bar under Ar (final P=30 bar).

The results appear in tables 4 and 5.

The analysis of the derivatives of glycerol is expressed in a similar manner to that of the preceding examples. The analysis of the fatty products present at the end of the reaction is expressed according to the following equations.

Triglyceride conversion: $Tri=100 \times (Tri_o - Tri_f)/Tri_o$ or $\Sigma yld_i$ Fatty acid ethyl ester yield: Ester yld=(⅓)×(Ester/$Tri_o$)

Monoglyceride yield: monoGly yld=(⅓)×(monoGly/$Tri_o$)

Diglyceride yield: diGly yld=(⅔)×(diGly/$Tri_o$)

The yields are corrected for the number of fatty chains.

TABLE 4

Analysis of the fatty products present at the end of the reaction

| | Ethyl esters | | | | Glycerides | | | |
|---|---|---|---|---|---|---|---|---|
| Products | C16 esters | C18 esters | C20 esters | C22 esters | Fatty acid mono-glyceride | Fatty acid di-glyceride | Fatty acid tri-glyceride | |
| No. of moles | 0.00146 | 0.02544 | 0.00092 | 0.00014 | 0.0015 | 0.00022 | — | |
| Yld (% mol) | 5 | 83 | 3 | 0.5 | 5 | 1 | — | $\Sigma yld_i = 98\%$ |

TABLE 5

Analysis of the derivatives of glycerol present at the end of the reaction
$Gly_o = Tri_o = 0.01144$ mol

| Products | Glycerides | | Glycerol ether | | | | |
|---|---|---|---|---|---|---|---|
| | Fatty acid mono-glyceride | Fatty acid diglyceride | 2-Ethoxy glycerol ether | 3-Ethoxy glycerol ether | 1,2-Ethoxy glycerol ether | 1,3-Ethoxy glycerol ether | |
| No. of moles | 0.0015 | 0.00022 | 0.00046 | 0.000256 | 0.00016 | 0.00016 | |
| Yld (% mol) | 13 | 2 | 4 | 22.5 | 1.5 | 1.5 | $\Sigma yld_i = 45\%$ |

EXAMPLE 4

Reaction Between Rapeseed Oil and Ethanol in the Presence of $Cs_2HPW_{12}O_{40}$ in Order to Produce, in a Single Step, Ethyl Esters of Fatty Acids (Biodiesel) and Glycerol Ethers (Fuel Ethers)

Tr=85° C. for 5 h, then Tr=200° C. for 6 h.

The reaction conditions were the following. 0.5 g of $Cs_2HPW_{12}O_{40}$ catalyst was used (pretreatment: 1 h under vacuum at 200° C.). 0.2051 mol of ethanol and 0.01138 mol (which corresponds to $Tri_o$ in the equations which follow) of rapeseed oil were used. The ethanol/ester molar ratio was 6 (the ethanol/oil molar ratio was 18). The rate of stirring was 500 rpm. The temperature was 85° C. for 5 hours then 200° C. for 6 hours. The autoclave was pressurized at 17 bar under Ar (final P=30 bar).

The results appear in tables 6 and 7.

EXAMPLE 5

Reaction Between Sunflower Oil and Ethanol in the Presence of $Cs_2HPW_{12}O_{40}$ in Order to Produce, in a Single Step, Ethyl Esters of Fatty Acids (Biodiesel) and Glycerol Ethers (Fuel Ethers)

Tr=85° C. for 5 h, then Tr=200° C. for 6 h.

The reaction conditions were the following. 0.5 g of $Cs_2HPW_{12}O_{40}$ catalyst was used (pretreatment: 1 h under vacuum at 200° C.). 0.2052 mol of ethanol and 0.01138 mol (which corresponds to $Tri_o$ in the equations which follow) of sunflower oil were used. The ethanol/ester molar ratio was 6 (the ethanol/oil molar ratio was 18). The rate of stirring was 500 rpm. The temperature was 85° C. for 5 hours then 200° C. for 6 hours. The autoclave was pressurized at 17 bar under Ar (final P=30 bar).

The results appear in tables 8 and 9.

TABLE 6

Analysis of the fatty products present at the end of the reaction

| Products | Ethyl esters | | | | Glycerides | | |
|---|---|---|---|---|---|---|---|
| | C16 esters | C18 esters | C20 esters | C22 esters | Fatty acid mono-glyceride | Fatty acid di-glyceride | Fatty acid tri-glyceride |
| No. of moles | 0.00158 | 0.02645 | 0.00097 | 0.00014 | 0.0015 | 0.00062 | — |
| Yld (% mol) | 5 | 77.5 | 3 | 0.5 | 4 | 4 | — |

$\Sigma yld_i = 94\%$

TABLE 7

Analysis of the derivatives of glycerol present at the end of the reaction
$Gly_o = Tri_o = 0.01138$ mol

| Products | Glycerides | | Glycerol ether | | | | |
|---|---|---|---|---|---|---|---|
| | Fatty acid mono-glyceride | Fatty acid diglyceride | 2-Ethoxy glycerol ether | 3-Ethoxy glycerol ether | 1,2-Ethoxy glycerol ether | 1,3-Ethoxy glycerol ether | |
| No. of moles | 0.0015 | 0.00062 | 0.00048 | 0.000274 | 0.00027 | 0.00028 | |
| Yld (% mol) | 13.2 | 5.5 | 4.2 | 24 | 2.5 | 2.5 | $\Sigma yld_i = 52\%$ |

TABLE 8

Analysis of the fatty products present at the end of the reaction

| Products | Ethyl esters | | | | Glycerides | | |
|---|---|---|---|---|---|---|---|
| | C16 esters | C18 esters | C20 esters | C22 esters | Fatty acid mono-glyceride | Fatty acid di-glyceride | Fatty acid tri-glyceride |
| No. of moles | 0.00217 | 0.02645 | 0.00084 | 0 | 0.0014 | 0.00066 | — |
| Yld (% mol) | 6 | 77.5 | 2.5 | 0.5 | 4 | 4 | — $\Sigma yld_i = 94.5\%$ |

TABLE 9

Analysis of the derivatives of glycerol present at the end of the reaction
$Gly_o = Tri_o = 0.01138$ mol

| Products | Glycerides | | Glycerol ether | | | |
|---|---|---|---|---|---|---|
| | Fatty acid mono-glyceride | Fatty acid diglyceride | 2-Ethoxy glycerol ether | 3-Ethoxy glycerol ether | 1,2-Ethoxy glycerol ether | 1,3-Ethoxy glycerol ether |
| No. of moles | 0.0014 | 0.00066 | 0.00071 | 0.000254 | 0.00017 | 0.00017 |
| Yld (% mol) | 12.2 | 5.8 | 6.2 | 22.3 | 1.5 | 1.5 $\Sigma yld_i = 49.5\%$ |

The invention claimed is:

1. A method for the etherification of glycerol by ethanol comprising reacting glycerol and ethanol in the presence of a catalyst comprising at least one alkali metal or ammonium heteropoly acid salt having a differential heat of adsorption of ammonia greater than or equal to 150 kJ/mol, and being stable at T>150° C.

2. The method as claimed in claim 1, wherein the catalyst comprising at least one alkali metal or ammonium heteropoly acid salt has a differential heat of adsorption of ammonia greater than or equal to 170 kJ/mol.

3. The method as claimed in claim 1, wherein the heteropoly acid salt is a salt of the heteropoly acids having the general formula:

$$H_k X_l M_m O_n \cdot x H_2O$$

in which:
X represents a heteroatom chosen from the group constituted by the following elements: P, Si, Ge, B or As;
M represents a peripheral metallic element chosen from the group constituted by W, Mo or V;
l is the number of heteroatoms and represents 1 or 2;
k is the number of hydrogen atoms and is between 1 and 10;
m is the number of peripheral metallic atoms W, Mo, V and is between 1 and 20;
n is the number of oxygen atoms and is between 2 and 62;
x is the number of molecules of water of hydration and is between 0 and 40.

4. The method as claimed in claim 1, wherein the heteropoly acid salt is a salt of a heteropoly acid selected from the group consisting of $H_3PW_{12}O_{40} \cdot 24H_2O$, $H_4SiW_{12}O_{40} \cdot 24H_2O$, $H_6P_2W_{18}O_{62} \cdot 24H_2O$, $H_5BW_{12}O_{40} \cdot 30H_2O$, $H_5PW_{10}V_2O_{40} \cdot xH_2O$, $H_3PMo_{12}O_{40} \cdot 28H_2O$, $H_4SiMo_{12}O_{40} \cdot 13H_2O$, $H_3PMo_6V_6O_{40} \cdot xH_2O$ and $H_5PMo_{10}V_2O_{40} \cdot xH_2O$.

5. The method as claimed in claim 4, wherein the salt is selected from the group consisting of alkali metal salts $Cs^+$, $K^+$ and $Rb^+$ and ammonium salts ($NH_4^+$).

6. The method as claimed in claim 1, wherein the method is carried out at a temperature between 100 and 300° C. and at a pressure between 5 and 100 bar.

7. The method according to claim 1 in which the glycerol is obtained by transesterification of a vegetable oil or animal oil by ethanol in the presence of a catalyst comprising at least one alkali metal or ammonium heteropolyacid salt having a differential heat of adsorption of ammonia greater than or equal to 150 kJ/mol and being stable at T>150° C.

8. The method according to claim 7, in which the molar ratio between the alcohol and the vegetable or animal oil is between 1 and 50.

9. The method according to claim 7, in which the catalyst is as defined in any one of claims 2, 3, 4, and 5.

10. The method according to claim 7 characterized in that it is carried out at a temperature between 100 and 300° C. and at pressure between 5 and 100 bar.

* * * * *